(12) United States Patent
Königer et al.

(10) Patent No.: US 6,177,379 B1
(45) Date of Patent: Jan. 23, 2001

(54) INITIATORS FOR RADICAL POLYMERIZATION

(75) Inventors: Rainer Königer, Ludwigshafen; Reinhold Schwalm, Wachenheim; Roman Benedikt Raether, Ludwigshafen, all of (DE)

(73) Assignee: BASF Aktiengesellschaft, Ludwigshafen (DE)

( * ) Notice: Under 35 U.S.C. 154(b), the term of this patent shall be extended for 0 days.

(21) Appl. No.: 09/080,239

(22) Filed: May 18, 1998

(51) Int. Cl.[7] ............ B01J 31/00; B01J 27/24; C07D 237/00; C07D 237/26; C08F 2/00

(52) U.S. Cl. ............ 502/162; 502/167; 502/150; 502/200; 544/244; 544/234; 544/235; 544/236; 526/217; 526/218.1; 526/219.1; 526/219.3; 526/220

(58) Field of Search ............ 502/150, 162, 502/167, 200; 544/224, 234, 235, 236; 526/217, 218.1, 219.1, 219.3, 220

(56) References Cited

U.S. PATENT DOCUMENTS

| 3,424,734 | * | 1/1969 | Schleimer et al. | 526/218.1 |
|---|---|---|---|---|
| 4,481,356 | * | 11/1984 | Gilbertson | 544/234 |
| 4,500,649 | * | 2/1985 | Tanaka et al. | 502/167 |
| 4,504,640 | * | 3/1985 | Harada et al. | 526/193 |
| 5,034,051 | * | 7/1991 | Kume et al. | 504/221 |

FOREIGN PATENT DOCUMENTS

| 42 07 558 A 1 | 9/1993 | (DE) . |
|---|---|---|
| WO 97/31901 | 9/1997 | (WO) . |

* cited by examiner

*Primary Examiner*—Mark L. Bell
*Assistant Examiner*—Patricia L. Hailey
(74) *Attorney, Agent, or Firm*—Oblon, Spivak, McClelland, Maier & Neustadt, P.C.

(57) ABSTRACT

A method of initiating free-radical addition polymerization, which entails effecting a free-radical addition polymerization in the presence of an initiator, which contains, as a structural feature, a Diels-Alder adduct of an azo group (—N=N—) with a conjugated double bond (diene).

7 Claims, No Drawings

INITIATORS FOR RADICAL POLYMERIZATION

BACKGROUND OF THE INVENTION

1. Field of the Invention

The invention relates to initiators for free-radical addition polymerization, comprising as structural feature the Diels-Alder adduct of an azo group (—N=N—) with a conjugated double bond (diene).

2. Description of the Background

Initiators for free-radical addition polymerization are compounds which decompose into free radicals and so initiate the free-radical addition polymerization. The rate of decomposition is generally dependent on temperature and can be described by the Arrhenius equation. Accordingly, decomposition to free radicals begins even at relatively low temperatures and is accelerated by temperature increase.

For some fields of use, for example for the curing of powder coatings, initiators are desired which become effective only at high temperatures. Following application to the substrate surface, powder coatings must generally be heated to flowability in order to obtain a smooth and level coating film. Curing (free-radically crosslinking), which begins simultaneously by decomposition of the initiators to free radicals, leads in this case to unevennesses or defects in the coating surface. Instead, curing should not begin until after a smooth coating film has been formed by the melting of the polymer powder.

This requires initiators which decompose to free radicals only at high temperatures. The temperature dependency of the rate of decomposition in this case should be as low as possible; in other words, no decomposition below a certain temperature as complete as possible a decomposition above this temperature (non-Arrhenius behavior).

SUMMARY OF THE INVENTION

The object of the present invention was to provide appropriate initiators.

Accordingly, the initiators defined at the outset have been found.

The initiators according to the invention comprise as structural feature the Diels-Alder adduct of an azo group, that is an —N=N— group, with a diene.

DETAILED DESCRIPTION OF THE PREFERRED EMBODIMENTS

A Diels-Alder reaction is a 1,4-cycloaddition of a C,C double bond (here an azo group instead) onto a conjugated double bond (diene).

Accordingly, the initiators according to the invention can be obtained by 1,4-cycloaddition of the azo group of an azo compound (dienophile) onto a diene.

The azo compound is a compound which is already an initiator for free-radical polymerization and which decomposes to free radicals above certain temperatures (azo initiator). Furthermore, the azo compound should be able to undergo a Diels-Alder reaction. Suitable azo compounds are, for example, those of the formula

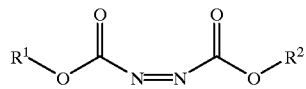

in which $R^1$ and $R^2$ independently of one another represent organic radicals.

The radicals $R^1$ and $R^2$ are preferably organic radicals which contain up to 30, in particular up to 20 C atoms and, if desired, also heteroatoms such as N, O, S.

With particular preference, $R^1$ and $R^2$ independently of one another are a $C_1$–$C_{20}$-alkyl group, a $C_5$–$C_{20}$-aryl group or cycloalkyl group, a $C_6$- to $C_{20}$-alkaryl or aralkyl group. In particular they are a $C_1$–$C_8$ alkyl group. The alkyl groups can be linear or branched.

Another azo compound capable of the Diels-Alder reaction is an imide of the formula

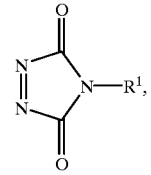

$R^1$ has the meaning indicated above.

The initiating action of the azodicarboxylic esters has been described in the literature (T. Schmelzer and J. Springer; Eur. Polym. J. 23(3), pp. 243–248 (1987)).

Examples of suitable dienes which form the Diels-Alder adduct with the azo compounds are butadiene, cyclopentadiene, cyclohexadiene, or derivatives thereof in which one or more of the hydrogen atoms are substituted by organic radicals.

All that is essential is that a conjugated double bond is present which is capable of a Diels-Alder reaction.

The implementation of the Diels-Alder reaction is known.

For preparing the initiators according to the invention it is possible to react the azo compounds with the diene, for example, at temperatures from 0° C. to 100° C. in a solvent.

In the reaction of the azo compounds of the formula Ia, for example with cyclopentadiene, the following Diels-Alder adduct is obtained:

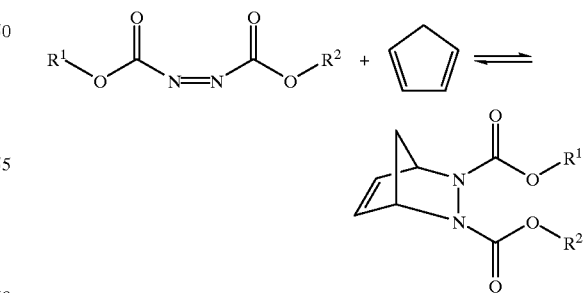

With the initiator according to the invention as well, the original azo compound is the compound which decomposes to free radicals and so acts initiatingly. All that is necessary is that this azo compound must first of all be released from the Diels-Alder adduct by a reversal of the Diels-Alder reaction (retro-Diels-Alder reaction).

The temperature which is required for the retro-Diels-Alder reaction depends on the choice of the azo compound with the diene components. In general, the temperatures lie above 100° C., in particular between 150 and 250° C. These temperatures generally lie above the decomposition temperature of the azo compounds. In the case of temperature increase, the azo compound is released only after the retro-Diels-Alder reaction has taken place, so that the temperature of decomposition of the initiators according to the invention to free radicals is higher than that of the original azo compounds.

The retro-Diels-Alder reaction also follows the Arrhenius Law, i.e. it shows a certain temperature dependency. A further improvement of this invention can be achieved if this temperature dependency is reduced still further.

The literature reference Frechet, J. M. J.; Eichler, E, HO, H; Willson C. G. Polymer 1996, 24, 995–1000 discloses that phenyl tert-butyl carbonate decomposes abruptly when heated into isobutene:

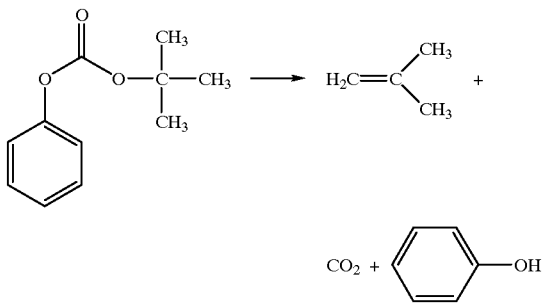

The decomposition is autocatalytic and does not follow the Arrhenius Law.

Corresponding addition of substituents onto the Diels-Alder adduct of the formula IIIa, for example, gives the compound IIIb

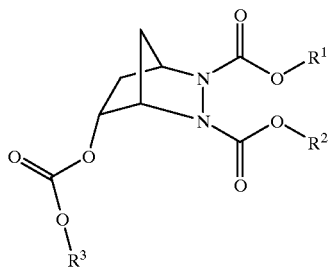

in which $R^3$ represents a phenyl group which may additionally carry further substituents.

The compound of the formula IIIb decomposes at elevated temperature autocatalytically, giving off $CO_2$ and eliminating phenol as it does so, to the Diels-Alder adduct of the formula IIIa, which then decomposes further in a retro-Diels-Alder reactor [sic] to the azo compound which is active as initiator. By this means the temperature dependency of the decomposition of the Diels-Alder adduct is suppressed and the initiator present in the Diels-Alder adduct becomes effective to its full extent only above the temperature of the autocatalytic decomposition.

Diels Alder adducts which are subject to such an autocatalytic decomposition are those which are substituted by at least one group of the formulae

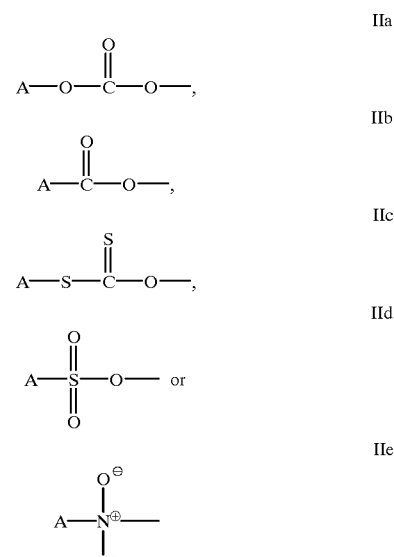

A and A' in the above formulae independently of one another represent organic radicals having 1 to 30 C atoms, preferably 2 to 20 C atoms.

The radical involved is in particular one which has an aromatic ring system. With particular preference it is a phenyl group, which may if desired carry further substituents, e.g. $C_1$–$C_8$ alkyl groups. Very particular preference is given to a phenyl group.

Preferred substituents are groups of the formula IIa or IId, especially phenylcarbonate or phenylsulfonate.

The Diels Alder adduct preferably contains one or two, with particular preference one substituent of the formula IIa to IIe.

The phenyl group of the phenylcarbonate or phenylsulfonate respectively may contain further substituents, in particular for example $C_1$–$C_8$ alkyl groups. By this means it is possible to vary the autocatalytic decomposition temperature.

The above groups of the formulae IIa) to IIe), especially the phenylcarbonate or phenylsulfonate group respectively can be attached to the Diels-Alder adduct, for example, by means of customary addition reaction onto the double bonds obtained in the course of the Diels-Alder reaction. Also particularly suitable are esterifications of the acids, acid anhydrides or acid chlorides derived from IIa to IIe with Diels-Alder adducts containing hydroxy groups. The attachment of the phenylcarbonate or phenylsulfonate group, or of derivatives thereof, is achieved with particular simplicity by reacting

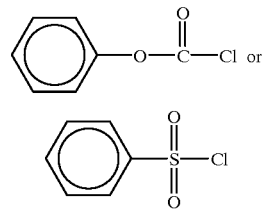

with Diels-Alder adducts containing hydroxy groups.

The initiators according to the invention are suitable as initiators for free-radical addition polymerization. This may involve the addition polymerization of low-molecular monomers, examples being acrylates, vinylaromatic compounds, vinyl esters, vinyl ethers, etc. Also suitable is the crosslinking of oligomers and polymers by free-radical addition polymerization of free-radically polymerizable, ethylenically unsaturated groups which are present in the polymer or oligomer. For example, polymers or oligomers may contain epoxide groups, which are reacted with acrylic acid or hydroxyalkyl acrylates, and so the desired content of double bonds is established. The initiators according to the invention are of particular interest for polymer powders which are crosslinked, or cured, by free-radical addition polymerization.

The content of the initiators according to the invention is in general from 0.05 to 10 parts by weight, in particular from 0.1 to 5 parts by weight, based on 100 parts by weight of the free-radically polymerizable monomers and/or free-radically crosslinkable oligomers or polymers that are present overall.

EXAMPLES

1. Preparing Initiators 1.1. Diels-Alder Adducts 1.1.1.

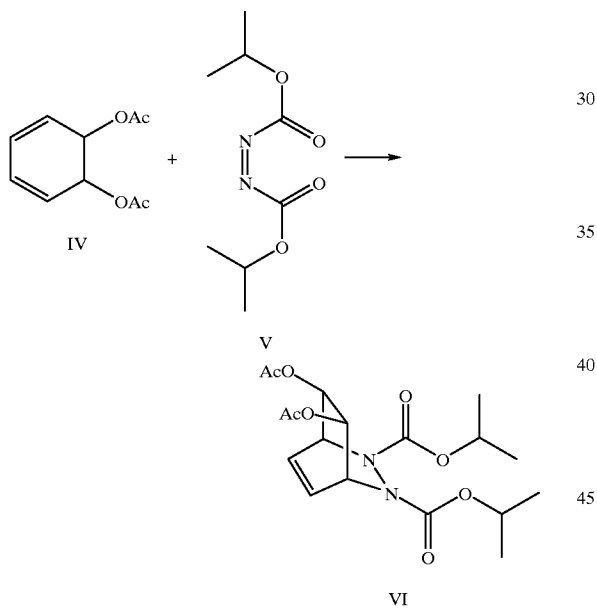

7.7 g of IV and 7.9 g of V are dissolved in 400 ml of cyclohexane and the solution is irradiated with UV light at 50° C. for 20 hours. After the reaction, the solvent is distilled off and the crude product is purified by chromatography. Yield: 6.2 g of VI.

1.1.2.

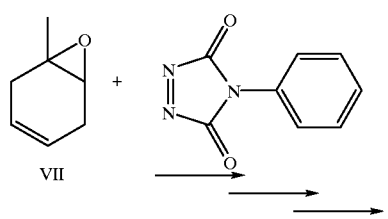

-continued

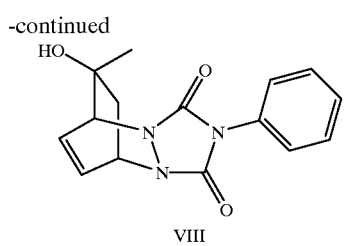

2.2 g of VII are dissolved in diethyl ether and the solution is added dropwise at 0° C. to a 1.4-molar solution of methyllithium in diethyl ether. The mixture is stirred for an hour at room temperature, and 10 ml of a 5% strength sodium hydroxide solution are added. The organic phase is washed with saturated sodium chloride solution, and 4-phenylurazole is added.

The solvent is distilled off and the intermediate is purified by chromatography. 1.6 g of a white solid are obtained. 3.27 g of chromium trioxide are dissolved in 80 ml of methylene chloride, and 5.2 g of pyridine are added with ice cooling. The abovementioned white solid, dissolved in 10 ml of methylene chloride, is added dropwise to this solution at 0° C. The mixture is stirred at room temperature for 1 hour and decanted. The solution is washed, dried and concentrated. The crude product is purified by chromatography and by recrystallization. Yield: 165 mg of VIII (white crystals).

1.1.3.

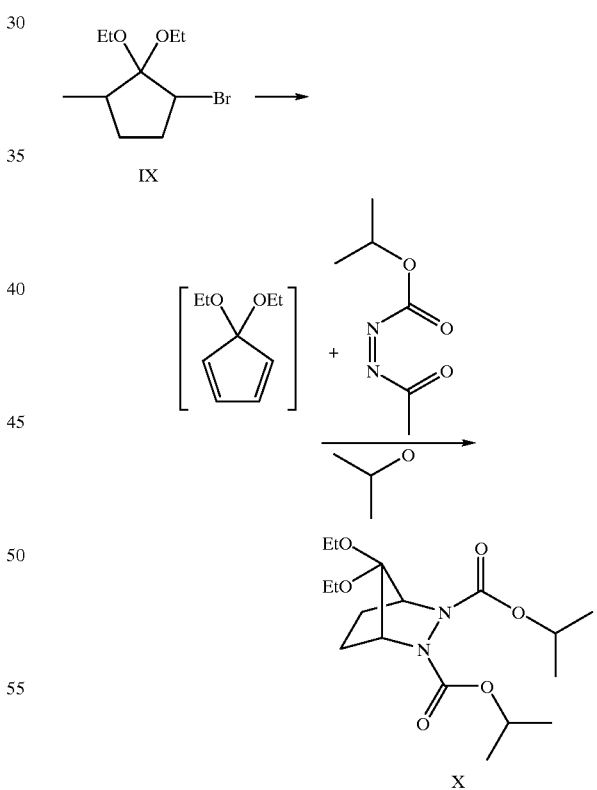

8.9 g of IX are dissolved in 25 ml of dimethyl sulfoxide, and this solution is added dropwise at 17° C. to a solution of 12.84 g of potassium t-butylate in 75 ml of dimethyl sulfoxide. 100 ml of cold pentane are added and the mixture is poured into 100 ml of ice. The organic phase is separated off, held at 0° C. and added dropwise over the course of one hour to a solution of 23.24 g of diisopropyl azodicarboxylate in 30 ml of diethyl ether. The solution is subsequently heated up to boiling for 2.5 h. The volatile constituents are distilled off and the yellow oil obtained is dissolved in n-hexane, the solution being stored in a refrigerator. 1.18 g of X (white crystals) emerge overnight.

1.1.4.

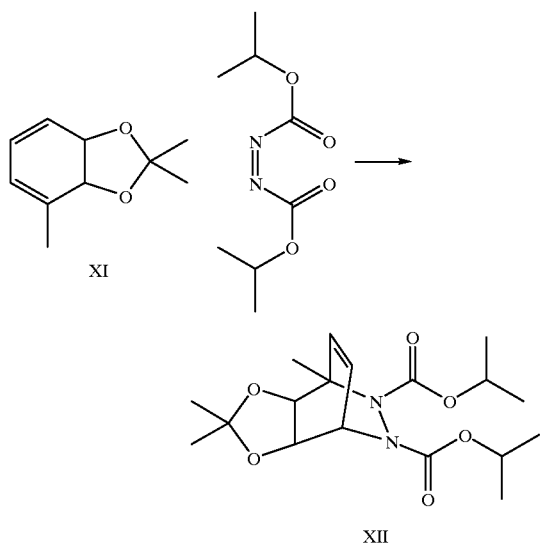

XI

XII 200 mg of XI and 200 mg of diisopropyl azodicarboxylate are dissolved in benzene and the solution is heated at boiling for 24 h. The solvent is distilled off and the crude product is purified by chromatography. Yield: 220 mg of XII (colorless oil).

1.1.5.

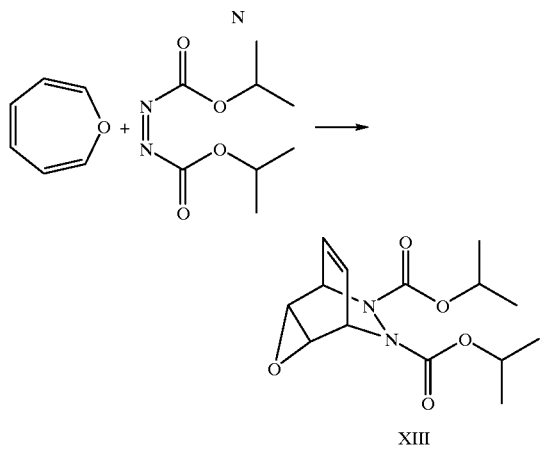

XIII 577 mg of oxepine are dissolved in 10 ml of chloroform, and 1210 mg of diisopropyl azodicarboxylate, dissolved in 4 ml of chloroform, are added over the course of 30 minutes. The mixture is stirred at room temperature for 21 h. The volatile constituents are distilled off and the residue is recrystallized. Yield: 1466 mg of XIII (white crystals).

1.1.6.

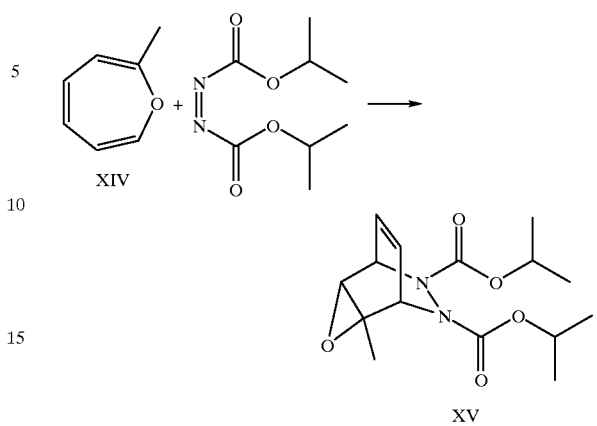

XIV

XV 560 mg of XIV are dissolved in 6 ml of chloroform, and 1070 mg of diisopropyl diazocarboxylate, dissolved in 2 ml of chloroform, are added. The mixture is stirred at room temperature for 24 h. The volatile constituents are distilled off and the residue is purified by chromatography. Yield: 710 mg of XV (colorless oil).

1.1.7.

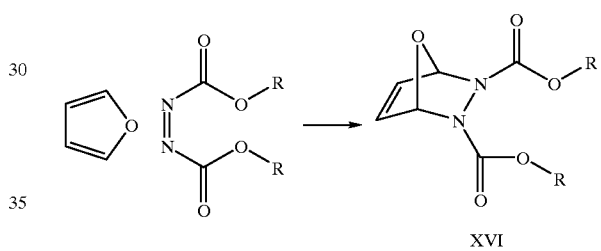

XVI 13.7 mmol of the corresponding dialkyl azodicarboxylate are dissolved in 10 ml of furan and the solution is stirred at room temperature for 20 h. Distillative removal of the volatile constituents leaves the product XVI (oil).

1.1.8.

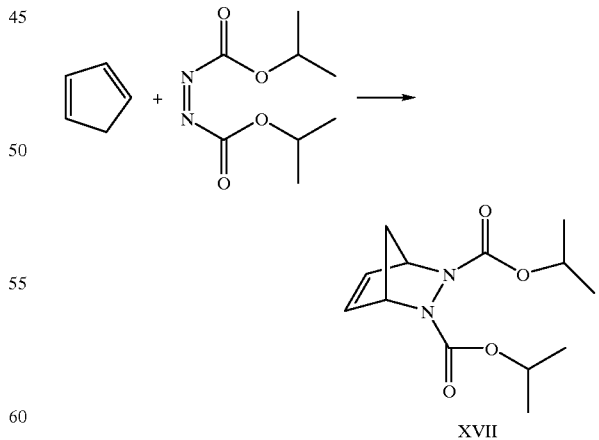

XVII

Cyclopentadiene is added dropwise to 3.22 g of ice-cold diisopropyl azodicarboxylate until the reaction solution has lost its color. The volatile constituents are distilled off and the residue is purified by chromatography. XVII is obtained as a colorless oil.

1.1.9.

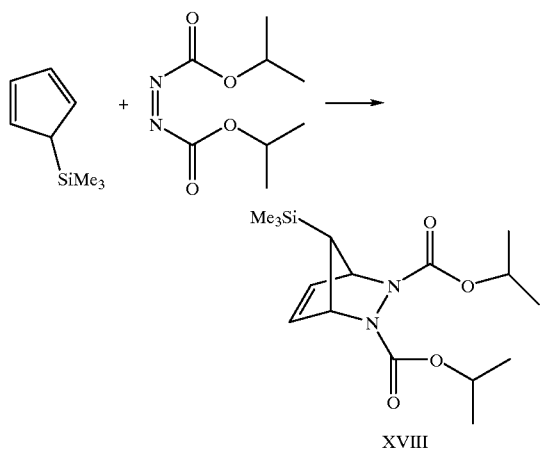

XVIII 7.8 ml of trimethylsilylcyclopentadiene and 6.71 g of diisopropyl azodicarboxylate are dissolved in tetrahydrofuran and the solution is stirred at room temperature for 18 h. The volatile constituents are distilled off and the residue is purified by chromatography. Yield: 3.51 g of XVIII (colorless oil).

1.2. Derivatizing the Described Diels-Alder Adducts
1.2.1.

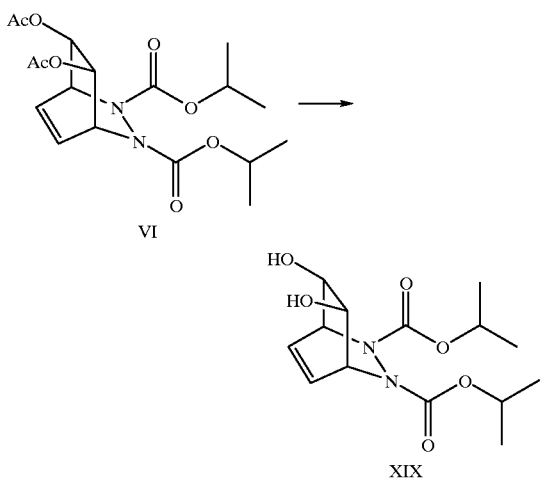

VI

XIX 220 mg of VI are dissolved in 10 ml of diethyl ether, and 51 mg of methanol and 35 mg of lithium borohydride are added. The mixture is heated at boiling for 2.5 h, neutralized and extracted. The organic phase is concentrated and the resulting oil is purified by chromatography. Yield: 36 mg of XIX (colorless oil).

1.2.2.

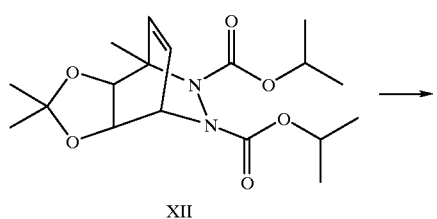

XII

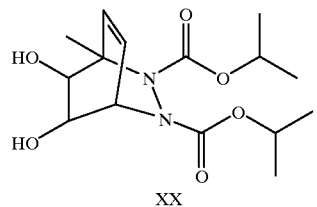

XX 220 mg of XII are dissolved in 10 ml of methanol, and a spatula tip of Amberlyst® 15 is added. The mixture is heated at 70° C. for 24 h. XX is obtained.

1.2.3.

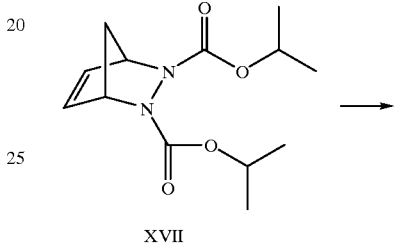

XVII

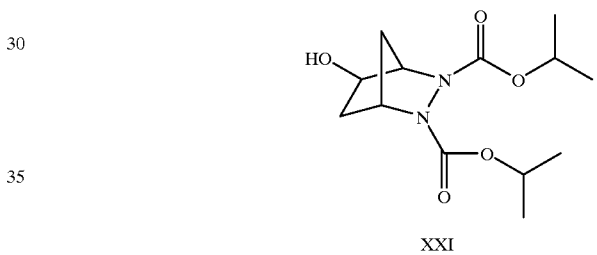

XXI 4.07 g of XVII are dissolved in 12 ml of tetrahydrofuran, the solution is cooled to 0° C. and 9.4 ml of a 1M borane solution are added. The solution is stirred for 1 h with cooling and for 2 h at room temperature. 2.8 ml of 3M sodium hydroxide solution and 2 ml of 30% hydrogen peroxide are added, and the solution is stirred at 0° C. for 30 minutes and at room temperature for 1 h. The solution is taken up in ethyl acetate and washed with saturated sodium chloride solution. The organic phase is concentrated and the crude product is purified by chromatography. Yield: 2.87 g of XXI (colorless oil, crystallizes after several days at room temperature).

1.2.4.

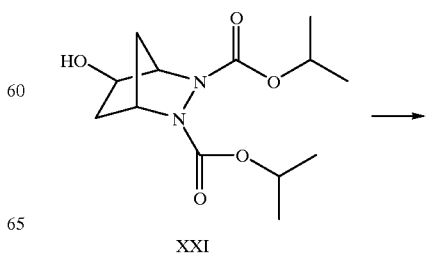

XXI

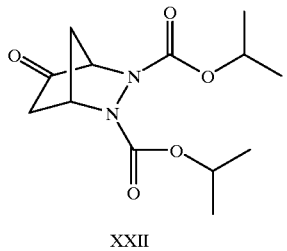

XXII 2.173 g of XXI are dissolved in 20 ml of methylene chloride, and 4.436 g of pyridinium dichromate, 8 g of molecular sieve and 0.8 ml of acetic acid are added. The mixture is stirred for 24 h and the filtrate is concentrated. The residue is taken up in diethyl ether, washed and concentrated. The crude product is purified by chromatography. Yield: 0.869 g of XXII (colorless oil, crystallizes after several days at room temperature).

1.2.5.

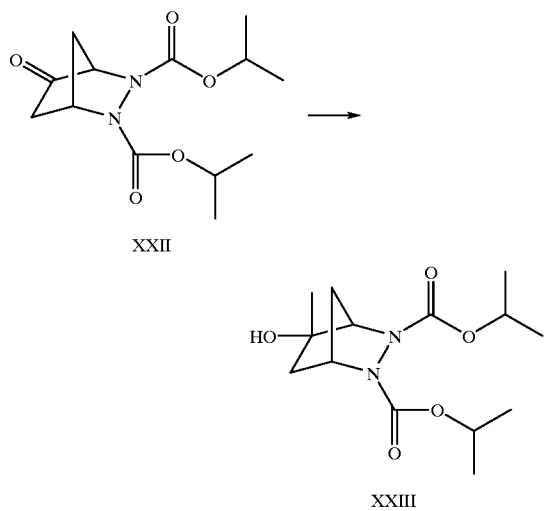

XXII

XXIII 0.106 g of XXII are dissolved in 9 ml of tetrahydrofuran, and 0.3 ml of a 3 M methylmagnesium chloride solution is added. The mixture is stirred for 2 h, ice is added, and the volatile constituents are distilled off. The residue is purified by chromatography. Yield: 0.02 g of XXIII (colorless oil).

1.2.6.

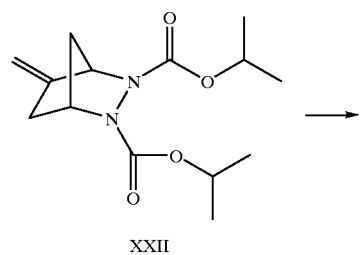

XXII

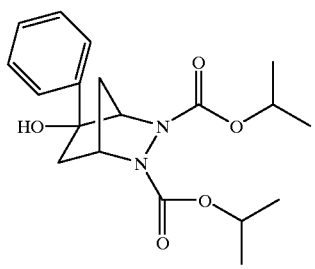

XXIV 0.116 g of XXII are dissolved in 10 ml of tetrahydrofuran, the solution is cooled to −78° C., and 0.465 ml of a 1M phenylmagnesium bromide solution is added. The solution is stirred at −78° C. for 2 h. Following the addition of ice and ethyl acetate, the organic phase is washed and concentrated. The crude product is purified by chromatography. Yield: 0.082 g of XXIV (yellowish oil).

1.3. Diels-Alder Adducts with Carbonate or Sulfonate Groups 1.3.1.

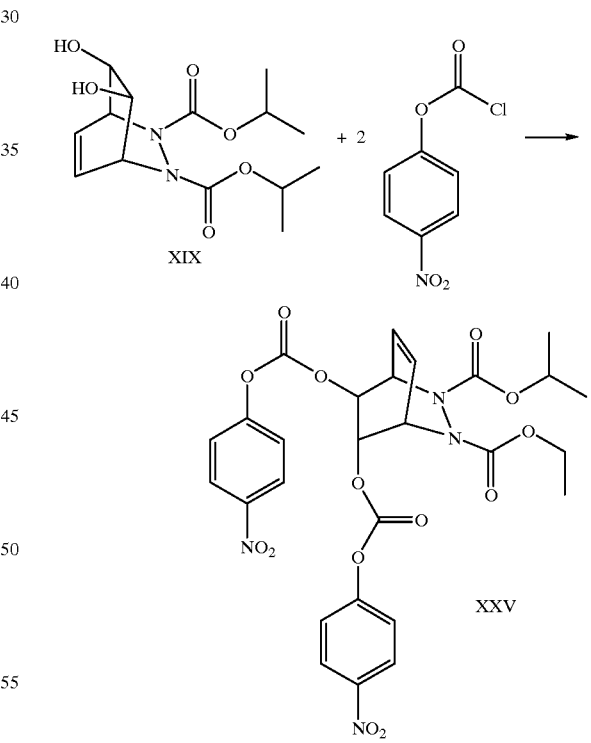

XIX

XXV 36 mg of XIX are dissolved in 2 ml of tetrahydrofuran, and 0.03 ml of pyridine is added. 46.4 mg of p-nitrophenyl chloroformate are added at 0° C. and the solution is stirred at room temperature for 17 h. Following the addition of 1 ml each of water and diethyl ether, the organic phase is separated off, washed and concentrated. The crude product is purified by chromatography. XXV is obtained.

1.3.2.

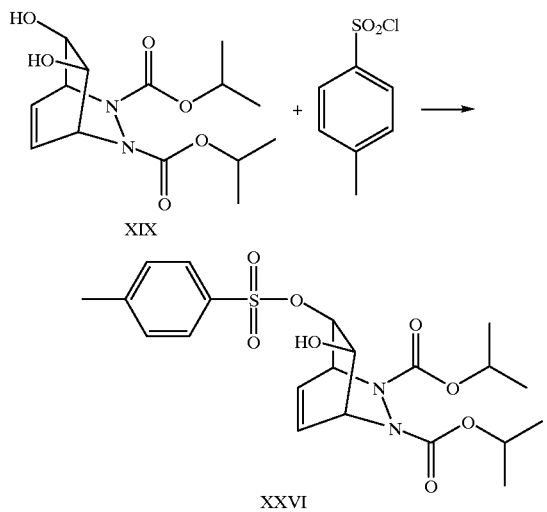

700 mg of XIX are dissolved in 10 ml of pyridine, and 425.4 mg of p-toluenesulfonyl chloride are added at 0° C. The solution is stored in the refrigerator for 2 d, then poured into 40 ml of ice containing hydrochloric acid. The organic phase is concentrated and the product is dried under a high vacuum. Yield: 720 mg of XXVI (white solid).

1.3.3.

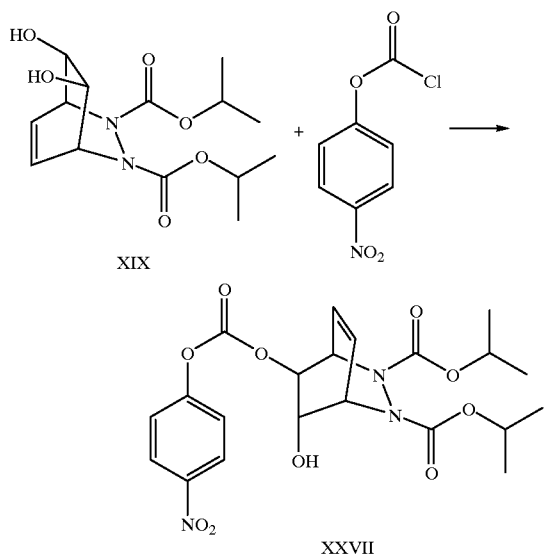

100 mg of XIX are dissolved in 20 ml of tetrahydrofuran, and 0.042 ml of pyridine is added. 63.5 mg of p-nitrophenyl chloroformate, dissolved in 6 ml of tetrahydrofuran, are added dropwise at 0° C. over the course of 50 minutes. The solution is stored in a refrigerator for 4.5 d, then 3 ml each of water and diethyl ether are added. The organic phase is washed and concentrated. The crude product is purified by chromatography. Yield: 70 mg of XXVII.

1.3.4.

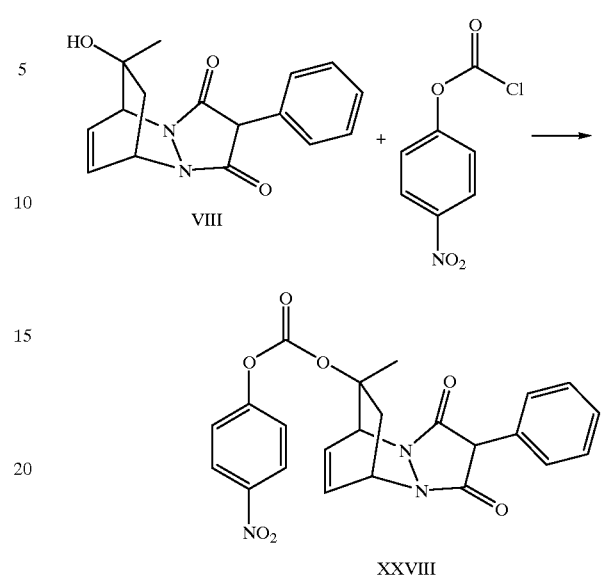

165 mg of VIII are dissolved in 7 ml of tetrahydrofuran, and 0.1 ml of pyridine is added. 121 mg of p-nitrophenyl chloroformate, dissolved in 3 ml of tetrahydrofuran, are added at 0° C. and the solution is stirred at 0° C. for 1.5 h and at room temperature for 17 h. Following the addition of 10 ml of diethyl ether and 5 ml of water, the organic phase is washed and concentrated. The crude product is purified by recrystallization. Yield: 105 mg of XXVIII (white solid).

1.3.5.

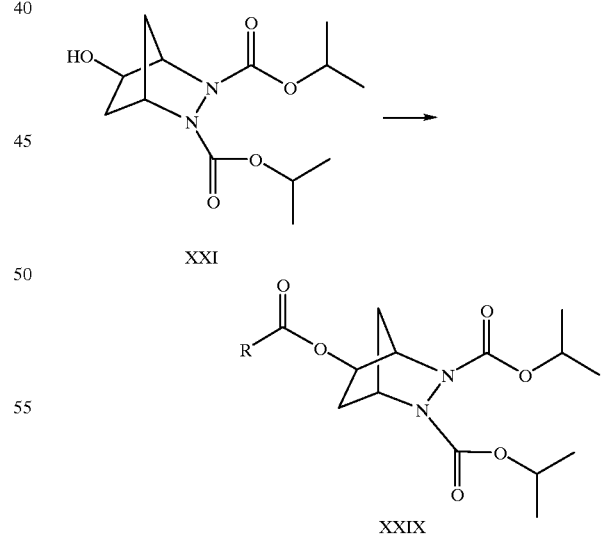

XXI is dissolved in the stated solvent, and a slight excess of the corresponding reactant is added. The mixture is stirred at room temperature, the volatile constituents are distilled off and the crude product is purified by chromatography.

| Reactant | R | Solvent/ catalyst | Reaction time [min] | Yield [%] |
|---|---|---|---|---|
| Carbonyl diimidazole | | Tetrahydrofuran | 1200 | 99 |
| Phenyl chloroformate | | Pyridine/ dimethylaminopyridine | 1080 | 97 |
| Methyl chloroformate | H₃C—O | Pyridine | 1440 | 9 |
| Isopropyl chloroformate | | Pyridine/ dimethylaminopyridine | 2880 | 13 |
| Potassium t-butoxide/ di-t-butyl dicarbonate | | Tetrahydrofuran | 180 | 72 |

1.3.6.

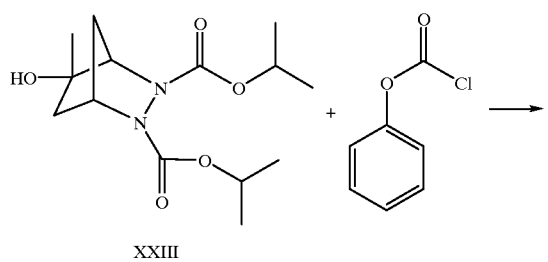

XXIII

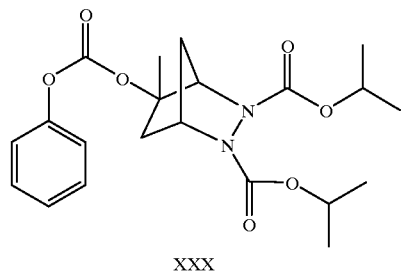

XXX 14.5 mg of XXIII are dissolved in 2.5 ml of methylene chloride, and 13.1 mg of dimethylaminopyridine and 0.035 ml of phenyl chloroformate are added in succession. The mixture is stirred at room temperature for 42 h. The volatile constituents are distilled off and the crude product is purified by chromatography. Yield: 15 mg of XXX (colorless oil).

2. Polymerizing 2.1. Polymerizing Without Initiator

Benzyl methacrylate was degassed under vacuum in a glass tube, sealed and heated in an oil bath at 150° C. for 1 hour. afterward, the viscosity had risen only slightly.

2.2. Polymerizing With Initiator 2.2.1. Polymerizing With XVII 2.2.1.1. With Benzyl Methacrylate Benzyl methacrylate and 5% by weight of XVII, based on benzyl methacrylate, were degassed under vacuum in a glass tube, sealed and heated in an oil bath at 150° C. for 1 hour. afterward, the mixture was no longer flowable.

2.2.1.2. With n-butyl Acrylate n-Butyl acrylate and 0.42% by weight of XVII, based on n-butyl acrylate, were degassed under vacuum in a glass tube, sealed and heated in an oil bath at 145° C. for 1 hour. Afterward, the batch was highly viscous.

3. Decomposition Temperatures 3.1. Decomposition Temperatures of Alkyl Phenyl Carbonates

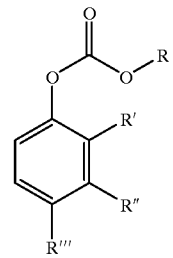

| Compound | R | R' | R'' | R''' | Decomposition temperature [° C.] |
|---|---|---|---|---|---|
| 1 | t-butyl | H | H | H | volatilizes >150 |
| 2 | t-butyl | H | NO₂ | H | 150 |
| 3 | t-butyl | Cl | H | Cl | volatilizes >170 |
| 4 | t-butyl | H | H | NO₂ | 65 |
| 5 | 2-propyl | H | H | NO₂ | volatilizes >250 |
| 6 | t-butyl | H | H | Cl | 140 |
| | t-butyl | | perfluoro | | volatilizes >80 |

3.2. Decomposition Temperatures of Diels-Alder Adducts With Carbonate or Sulfonate Group

| Compound | Decomposition temperature [° C.] |
|---|---|
| XXVI | 148 |
| XXVII | 170 |
| XXV | 195 |
| XXVIII | 245 |

What is claimed is:

1. An initiator for free-radical addition polymerization, which comprises, as a structural feature, a Diels-Alder adduct produced by reacting (a) a compound of the formula (Ia):

Ia)

with (b) a compound having a conjugated double bond (diene), wherein $R^1$ and $R^2$ are each organic radicals.

2. The initiator of claim 1, wherein said diene comprises butadiene, cyclopentadiene, or cyclohexadiene.

3. The initiator of claim 1, wherein said Diels-Alder adduct further contains at least one substituent selected from the group consisting of the following formulas:

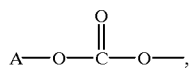   IIa

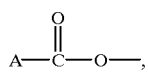   IIb

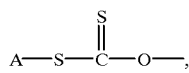   IIc

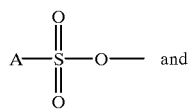 and   IId

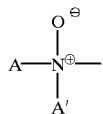   IIe wherein A and A' independently of each other represents an organic radical of from 1 to 30 carbon atoms.

4. The initiator of claim 3, wherein A and A' independently of each other represents an organic radical of from 2 to 20 carbon atoms.

5. The initiator of claim 1, wherein said organic radical comprises heteroatoms selected from the group consisting of N, O, and S.

6. The initiator of claim 1, wherein said organic radicals are selected from the group consisting of $C_1$–$C_{20}$-alkyl, $C_5$–$C_{20}$-aryl, $C_6$–$C_{20}$-alkaryl, and $C_6$–$C_{20}$-aralkyl.

7. The initiator of claim 1, wherein said organic radicals are each independently $C_1$–$C_8$ alkyl.

* * * * *